(12) United States Patent
Hojeibane

(10) Patent No.: US 6,423,091 B1
(45) Date of Patent: *Jul. 23, 2002

(54) HELICAL STENT HAVING FLAT ENDS

(75) Inventor: Hikmat Hojeibane, Princeton, NJ (US)

(73) Assignee: Cordis Corporation, Miami Lakes, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/571,230

(22) Filed: May 16, 2000

(51) Int. Cl.⁷ .................................................. A61F 2/06
(52) U.S. Cl. ...................................................... 623/1.15
(58) Field of Search ................................ 606/198, 194, 606/191; 623/1.11–1.16, 1.17–1.2, 1.22

(56) References Cited

U.S. PATENT DOCUMENTS

| | | |
|---|---|---|
| 4,733,665 A | 3/1988 | Palmaz |
| 5,135,536 A | 8/1992 | Hillstead ................... 623/1.15 |
| 5,810,872 A | 9/1998 | Kanesaka et al. .......... 623/1.15 |
| 5,824,059 A | 10/1998 | Wijay ........................ 623/1.15 |
| 5,913,897 A | 6/1999 | Corso, Jr. et al. |
| 6,042,597 A | 3/2000 | Kveen et al. ............... 623/1.15 |
| 6,117,165 A | 9/2000 | Becker ....................... 623/1.15 |
| 6,132,461 A | 10/2000 | Thompson ................. 623/1.15 |
| 6,190,406 B1 | 2/2001 | Duerig et al. .............. 623/1.15 |

*Primary Examiner*—Michael J. Milano
*Assistant Examiner*—(Jackie) Tan-Uyen T. Ho

(57) ABSTRACT

A helical stent having flat ends for insertion into a vessel of a patient provides a safe and effective means for ensuring the patency of the vessel. The stent comprises a tubular member having a thickness, front and back open ends, and a longitudinal axis extending therebetween. The tubular member includes a plurality of helically oriented continuous adjacent hoops extending between the front and back ends. The hoops have a plurality of longitudinal struts, each having opposing ends and a center therebetween, wherein the ends of the struts are shaped to form a plurality of loops connecting adjacent struts at the ends of the struts. The tubular member has end loops and the front and back ends thereof, wherein the end loops at each end are substantially aligned with each other along a plane substantially perpendicular to the longitudinal axis.

9 Claims, 2 Drawing Sheets

HELICAL STENT HAVING FLAT ENDS

FIELD OF THE INVENTION

The present invention relates to expandable intraluminal grafts ("stents") for use within a body passageway or duct which are particularly useful for repairing blood vessels narrowed or occluded by disease. The present invention relates even further to such stents having helically wound hoops.

BACKGROUND OF THE INVENTION

Various endoprosthesis assemblies which include expandable stents have been proposed or developed for use in association with angioplasty treatments and other medical procedures. The endoprosthesis assembly is percutaneously routed to a treatment site and the stent is expanded to maintain or restore the patency of a body passageway such as a blood vessel. A stent is typically cylindrical in shape comprising an expandable open frame. The stent will typically expand either by itself (self-expanding stents) or will expand upon exertion of an outwardly directed radial force on an inner surface of the stent frame by a balloon catheter or the like.

Stents for endovascular implantation into a blood vessel, artery or the like to maintain or restore the patency of the passageway have been deployed percutaneously to minimize the invasiveness associated with surgical exposure of the treatment site during coronary artery bypass. Percutaneous deployment is initiated by an incision into the vascular system of the patient, typically into the femoral artery. A tubular or sheath portion of an introducer is inserted through the incision and extends into the artery. The introducer has a central lumen which provides a passageway through the patient's skin and artery wall into the interior of the artery. An outwardly tapered hub portion of the introducer remains outside the patient's body to prevent blood from leaking out of the artery along the outside of the sheath. The introducer lumen includes a valve to block blood flow out of the artery through the introducer passageway. A distal end of a guide wire is passed through the introducer passageway into the patient's vasculature. The guide wire is threaded through the vasculature until the inserted distal end extends just beyond the treatment site. The proximal end of the guide wire extends outside the introducer.

For endovascular deployment, a stent, in an unexpanded or constricted configuration, is crimped onto a deflated balloon portion of a balloon catheter. The balloon portion is normally disposed near a distal end of the balloon catheter. The catheter has a central lumen extending its entire length. The distal end of the balloon catheter is threaded onto the proximal end of the guide wire. The distal end of the catheter is inserted into the introducer lumen and the catheter is pushed along the guide wire until the stent reaches the treatment site. At the treatment site, the balloon is inflated causing the stent to radially expand and assume an expanded configuration. When the stent is used to reinforce a portion of the blood vessel wall, the stent is expanded such that its outer diameter is approximately 10% to 20% larger than the inner diameter of the blood vessel at the treatment site, effectively causing an interference fit between the stent and the blood vessel that inhibits migration of the stent. The balloon is deflated and the balloon catheter is withdrawn from the patient's body. The guide wire is similarly removed. Finally, the introducer is removed from the artery.

An example of a commonly used stent is given in U.S. Pat, 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending force.

Other types of stents known in the art are often referred to as self expanding stents, which act like springs and will recover to their expanded or implanted configuration after being crushed. The prior art makes reference to the use of alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

One particular type of stent is often referred to as a helical stent, an example of which can be found in U.S. Pat. No. 5,913,897 issued to Corso et al. on Jun. 22, 1999, which is hereby incorporated herein by reference. A typical helical stent, such as the one disclosed in the Corso et al. reference, is made by either cutting a pattern from a solid tube or winding a wire around a mandrel. The tubular member has a plurality of adjacent helically aligned hoops extending between the front and back ends of the stent. The hoops are formed of a plurality of longitudinal struts, each having opposing ends and a center therebetween. The ends of the struts are shaped to form a plurality of loops, which connect adjacent struts at the ends of the struts. The stent further includes a plurality of bridges connecting adjacent hoops to one another. The endoprosthesis body is thus composed of a plurality of full-circle undulating hoops continuous with each other along the helical path. In general, the undulations of adjoining full circle hoops generally line up with one another to either contact one another or be closely spaced from one another. At selected ones of these locations, bridges are provided in order to join adjacent hoops. In the Corso et el. device, at least one bridge is positioned along each full-circle section, and the bridges are oriented with respect to each other so as to form a helical pattern of bridges along the endoprosthesis.

One disadvantage with prior art helical stents, is that the ends of the stent are not flat. That is, the end of the stent did not lie in a single plane substantially perpendicular to the longitudinal axis of the stent. The angled or beveled end configuration of the stent could result in a lift-up of the end loops while the stent is being delivered through very angled vessel curvatures. The lift-up could scrape the vessel wall causing injury to the vessel wall, or could prevent the stent from being advanced into the target area. Equally, the stent's proximal end could hang up upon retraction into the guide catheter, thus causing the stent to embolize.

SUMMARY OF THE INVENTION

In accordance with the present invention, there is provided a stent for insertion into a vessel of a patient. The stent is a tubular member having a thickness and having front and back open ends and a longitudinal axis extending therebetween. The member has a first smaller diameter for insertion into the vessel, and a second larger diameter for deployment into the vessel. The tubular member includes a plurality of helically oriented continuous adjacent hoops extending between the front and back ends. The hoops have a plurality of longitudinal struts each having opposing ends and a center therebetween, wherein the ends of the struts are shaped to form a plurality of loops connecting adjacent struts at the ends of the struts. The tubular member has end loops at the front and back ends thereof, wherein the end loops at each end are substantially aligned with each other along a plane substantially perpendicular to the longitudinal axis.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE INVENTION

Figure 1:
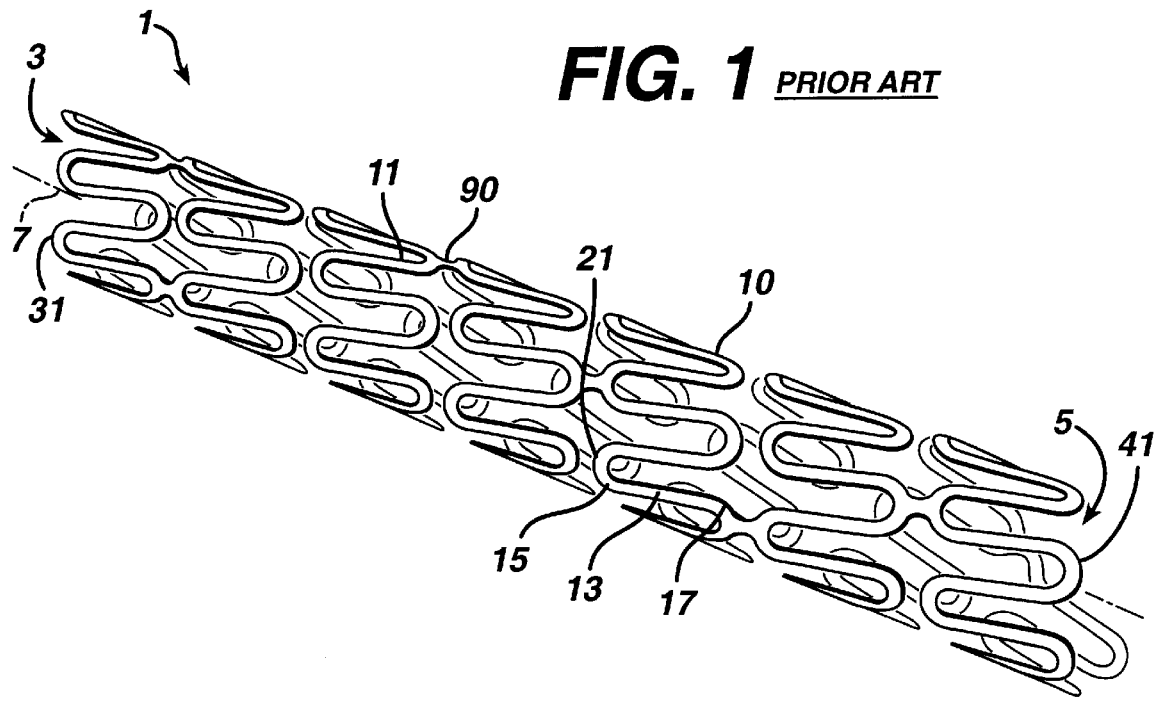
FIG. 1 is a side view of a prior art helical stent.
Figure 2:
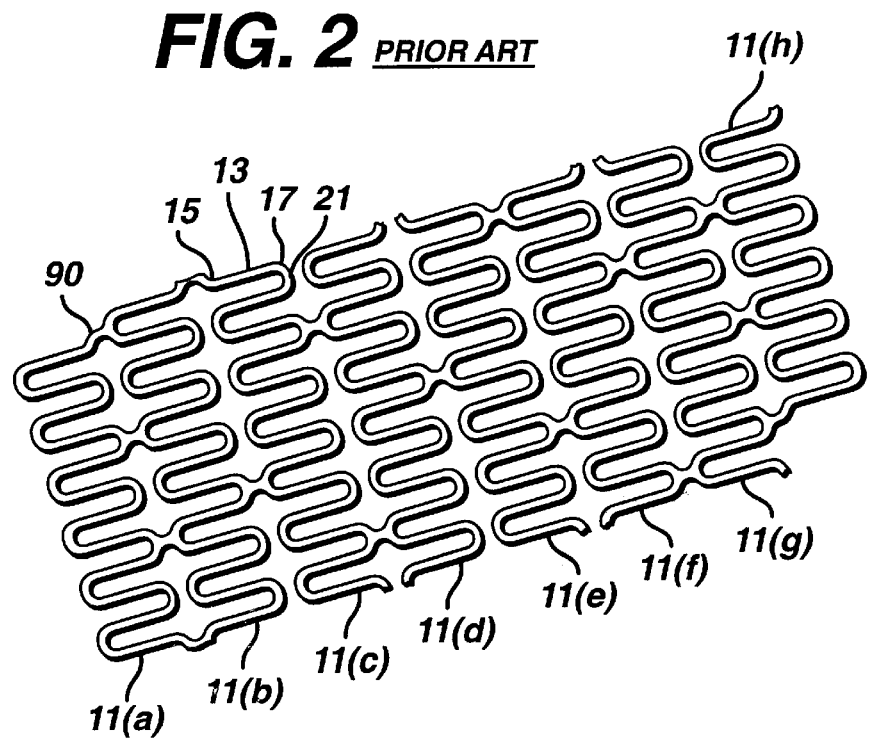
FIG. 2 is a plan view of the stent shown in FIG. 1 after such stent has been slit longitudinally and unrolled.

Referring now to the figures wherein like numerals indicate the same element throughout the views, there is shown in FIGS. 1 and 2 a prior art helical stent 1. The stent comprises a tubular 10 member having a thickness and having front and back open ends 3 and 5 and a longitudinal axis 7 extending therebetween. The member has a first smaller diameter for insertion into the vessel (shown in FIG. 1), and a second larger diameter for deployment into the vessel (not shown). The tubular member includes a plurality of helically oriented continuous adjacent hoops 11(a)–11(h) extending between the front and back ends. The hoops have a plurality of longitudinal struts 13 each having opposing ends 15 and 17 and a center therebetween. The ends of the struts are shaped to form a plurality of loops 21 connecting adjacent struts at the ends thereof Adjacent hoops are connected together by bridges 90.

The tubular member has end hoops 11(a) and 11(h) at the front and back ends thereof, wherein each end hoop has a plurality end loops 31 and 41. As seen from the figures, if one were to roll the planer member shown in FIG. 2 in such a way to have a helical configuration, shown in FIG. 1, the end loops 31 and 41 are not aligned with each other, giving the ends of the stent a pointed or angled configuration. This angled end could result in a lift-up of the end loops of the bevel during very angled vessel curvatures. The lift-up could scrape the vessel wall causing injury to the vessel wall, or could prevent the stent from being advanced into the stenosis. Equally, the stent's back end could hang up upon retraction into the guide at its beveled end, thus causing the stent to embolize.

Figure 3:
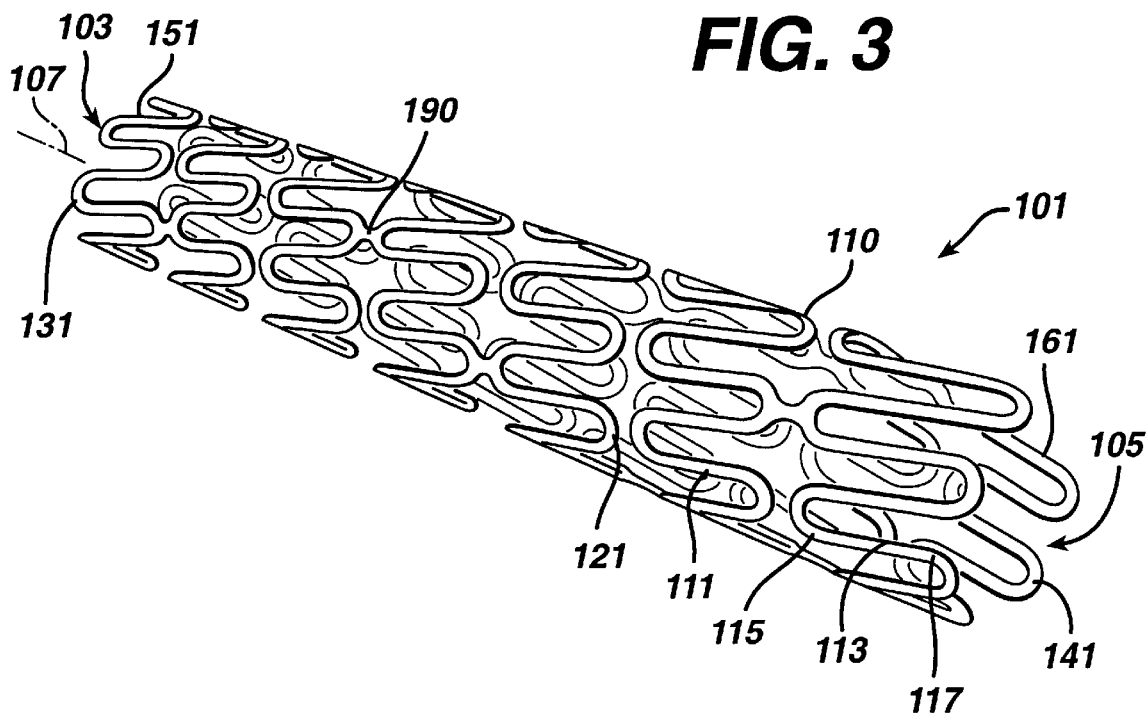
FIG. 3 is a side view of a stent made in accordance with the present invention.
Figure 4:
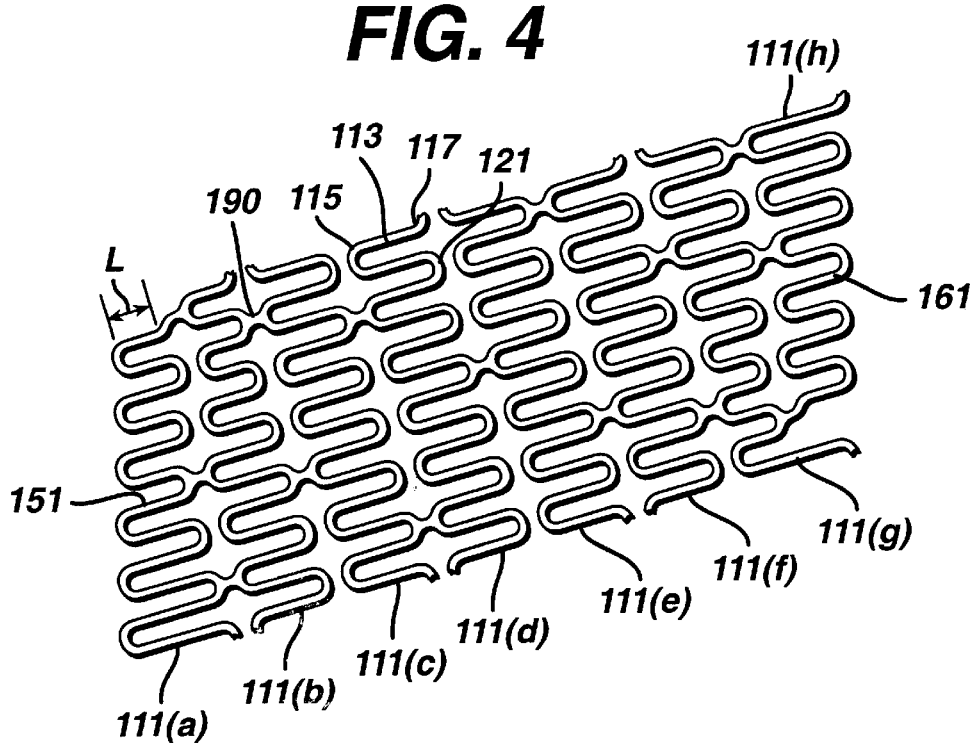
FIG. 4 is a view similar to that of FIG. 2, but showing the stent of FIG. 3 in its unrolled state.

FIGS. 3 and 4 show a stent 101 made in accordance with the present invention, which overcomes the above mentioned disadvantages. The stent comprises a tubular member 110 having a thickness and having front and back open ends 103 and 105 and a longitudinal axis 107 extending therebetween. The member has a first smaller diameter for insertion into the vessel (shown in FIG. 3), and a second larger diameter for deployment into the vessel (not shown). The tubular member includes a plurality of helically oriented continuous adjacent hoops 111(a)–111(h) extending between the front and back ends. The hoops have a plurality of longitudinal struts 113 each having opposing ends 115 and 117 and a center therebetween. The ends of the struts are shaped to form a plurality of loops 121 connecting adjacent struts at the ends thereof. Adjacent hoops are connected by bridges 190.

The tubular member has end hoops 111(a) and 111(h) at the front and back ends thereof, wherein each end hoop has a plurality end loops 131 and 141. End hoops 111(a) and 111(h) each have end struts 151 and 161 associated therewith, with each end loop having a length L. As seen from FIG. 4, the lengths of the end struts vary, preferably continuously from long to short around the end hoops. This varying in length of the end struts gives the helical stent 101 a flat end as shown in FIG. 3. That is the end loops 131 and 141 are substantially aligned with each other along a plane substantially perpendicular to the longitudinal axis. There is no angled or beveled end to the stent. That is the end loops 131 and 141 are substantially aligned with each other along a plane substantially perpendicular to the longitudinal axis. There is no angled or beveled end to the stent.

However, changing the length of the struts may affect the expansion uniformity of the stent at the front and back ends of the stent. Areas having shorter struts may expand very little, which could cause other areas of the stent to compensate and over-expand. This compensation phenomenon could not only result in a non-symmetrical expansion, but could also add high strains to the struts that over-expand. To compensate for this phenomenon, an adjustment of the location of the bridges 190 adjacent to the front and back ends of the stent may be undertaken. The bridges on the ends of the stent are strategically located to provide a sequence of connections between adjacent hoops. The end hoops 111(a) and 111(h) each have three bridges connecting them to the adjacent hoop 111(b) and 111(g) with, going from the top of the drawing down, the first bridge separated from the second bridge by two pairs of unbridged loops, and the second bridge separated from the third bridge by one pair of unbridged loops. The next set of end hoops 111(b) and 111(f) each have two bridges connecting them to the adjacent hoop 111(c) and 111(e) with the first bridge separated from the second bridge by two pairs of unbridged loops. Thereafter, as one follows the helical path of the hoops around the stent, each bridge is separated by three pairs of unbridged loops, until the path reaches the second outermost set of bridges connecting 111(b) and 111(f) to 111(c) and 111(e) respectively. This sequence can be described numerically as 21123 . . . This sequence of numbers denotes the location of the bridges on both ends of the stent. It means as you travel along the helical path of hoops, the first bridge is located on a first strut, the second bridge is located two pairs of unbridged loops past the first bridge, the third bridge is located one pair of unbridged loops past the second bridge, the fourth bridge is located one pair of unbridged loops past the: third bridge, the fifth bridge is located two pairs of unbridged loops past the fourth bridge, and the sixth bridge is located three pairs of unbridged loops past the fifth bridge, etc.

Preferably, stent 101 is made from stainless steel or nitinol tubing and laser cut with the desired pattern shown in the figures. However, it could be made from any number of materials known in the art, such as nitinol or tantalum, and any number of manufacturing methods known in the art, such as wire winding around a mandrel. In addition, as is known in the art, the stent could include a number of radiopaque markers, such as coating certain struts with a radiopaque material such as gold or tantalum.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A stent for insertion into a vessel of a patient, said stent comprising;
   a) a tubular member having a thickness and having front and back open ends and a longitudinal axis extending therebetween, said member having a first smaller diameter for insertion into said vessel, and a second larger diameter for deployment into said vessel; and
   b) said tubular member comprising a plurality of helically oriented continuous adjacent hoops extending between said front and back ends, said hoops comprising a plurality of longitudinal struts each having opposing ends wherein said ends of said struts are shaped to form a plurality of loops connecting adjacent struts, said tubular member having end loops at said front and back ends thereof, wherein said end loops at each end are substantially aligned with each other along a plane substantially perpendicular to said longitudinal axis, adjacent hoops are connected together by bridges at loops, the number of struts between bridges vary along the length of the stent such that the number of pairs of unbridged loops between bridges, from the front and back ends, vary in a symmetrical pattern until the number of pairs of unbridged loops reach steady state in a central portion of the tubular member, the number of pairs of unbridged loops start at a first number, decrease to a second number, remain at the second number, increase to the first number and then increase further to a third steady state number.

2. The stent according to claim 1, wherein said stent is made from stainless steel.

3. The stent according to claim 1, wherein said stent is made from nickel titanium alloy.

4. The stent according to claim 1 wherein at least a portion of the stent is substantially radiopaque.

5. A stent for insertion into a vessel of a patient, said stent comprising;
   a) a tubular member having a thickness and having front and back open ends and a longitudinal axis extending therebetween, said member having a first smaller diameter for insertion into said vessel, and a second larger diameter for deployment into said vessel; and
   b) said tubular member comprising a plurality of helically oriented continuous adjacent hoops extending between said front and back ends, said hoops comprising a plurality of longitudinal struts each having opposing ends wherein said ends of said struts are shaped to form a plurality of loops connecting adjacent struts, said tubular member having end hoops with end struts at said front and back ends of said tubular member, wherein said end struts have varying lengths, adjacent hoops are connected together by bridges at loops, the number of struts between bridges vary along the length of the stent such that the number of pairs of unbridged loops between bridges, from the front and back ends, vary in a symmetrical pattern until the number of pairs of unbridged loops reach steady state in a central portion of the tubular member, the number of pairs of unbridged loops start at a first number, decrease to a second number, remain at the second number, increase to the first number and then increase further to a third steady state number.

6. The stent according to claim 5 wherein said lengths of said end struts vary continuously from longer to shorter.

7. The stent according to claim 5, wherein said stent is made from stainless steel.

8. The stent according to claim 5, wherein said stent is made from nickel titanium alloy.

9. The stent according to claim 5 wherein at least a portion of the stent is substantially radiopaque.

* * * * *